United States Patent

Behrens et al.

(10) Patent No.: US 9,044,534 B2
(45) Date of Patent: Jun. 2, 2015

(54) MANUAL BREAST PUMP

(71) Applicants: Siska Behrens, Bremen (DE); Reinhold Jäger-Waldau, Scheessel (DE)

(72) Inventors: Siska Behrens, Bremen (DE); Reinhold Jäger-Waldau, Scheessel (DE)

(73) Assignee: MAPA GmbH, Zeven (DE)

(*) Notice: Subject to any disclaimer, the term of this patent is extended or adjusted under 35 U.S.C. 154(b) by 0 days.

(21) Appl. No.: 14/025,141

(22) Filed: Sep. 12, 2013

(65) Prior Publication Data

US 2014/0088495 A1 Mar. 27, 2014

(30) Foreign Application Priority Data

Sep. 14, 2012 (DE) .................... 20 2012 008 803 U

(51) Int. Cl.
A61M 1/06 (2006.01)
A61M 1/00 (2006.01)

(52) U.S. Cl.
CPC ............... A61M 1/06 (2013.01); A61M 1/0072 (2014.02); A61M 1/064 (2014.02); A61M 2205/075 (2013.01); A61M 2205/071 (2013.01); A61M 1/066 (2014.02)

(58) Field of Classification Search
CPC ............................. A61M 1/06; A61M 1/0072
USPC .................................. 604/73, 74, 75, 76, 346
See application file for complete search history.

(56) References Cited

U.S. PATENT DOCUMENTS

| 2004/0039330 | A1* | 2/2004 | Silver .............................. 604/74 |
| 2004/0087898 | A1 | 5/2004 | Weniger |
| 2004/0249340 | A1* | 12/2004 | Britto et al. ..................... 604/74 |
| 2005/0154348 | A1 | 7/2005 | Lantz et al. |
| 2010/0262072 | A1* | 10/2010 | Attolini et al. .................. 604/74 |
| 2010/0324479 | A1* | 12/2010 | Kliegman et al. ............... 604/74 |

FOREIGN PATENT DOCUMENTS

EP 2 138 197 A1 12/2009

* cited by examiner

Primary Examiner — Rebecca E Eisenberg
Assistant Examiner — Anh Bui
(74) Attorney, Agent, or Firm — Vidas, Arrett & Steinkraus, P.A.

(57) ABSTRACT

A breast milk pump that is easier to disassemble for cleaning and is easier to reassemble. It includes a housing, a cup-like displacement chamber a connection channel and a milk collection container releasably attached. A suction bell is connected to an inlet of the connection channel. It further includes a cup-like membrane element and a coupling element and a lever with rotatable mounting.

19 Claims, 8 Drawing Sheets

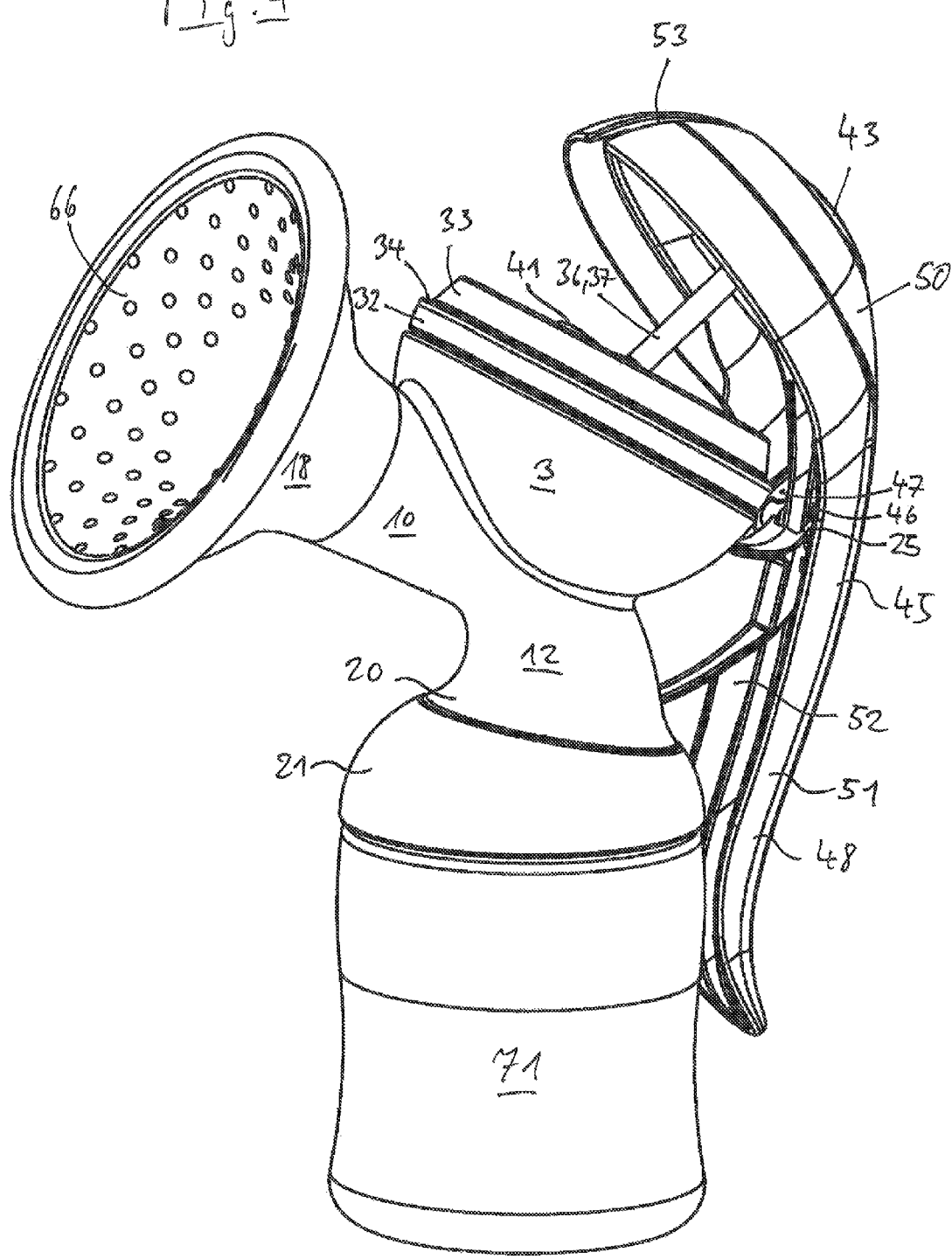

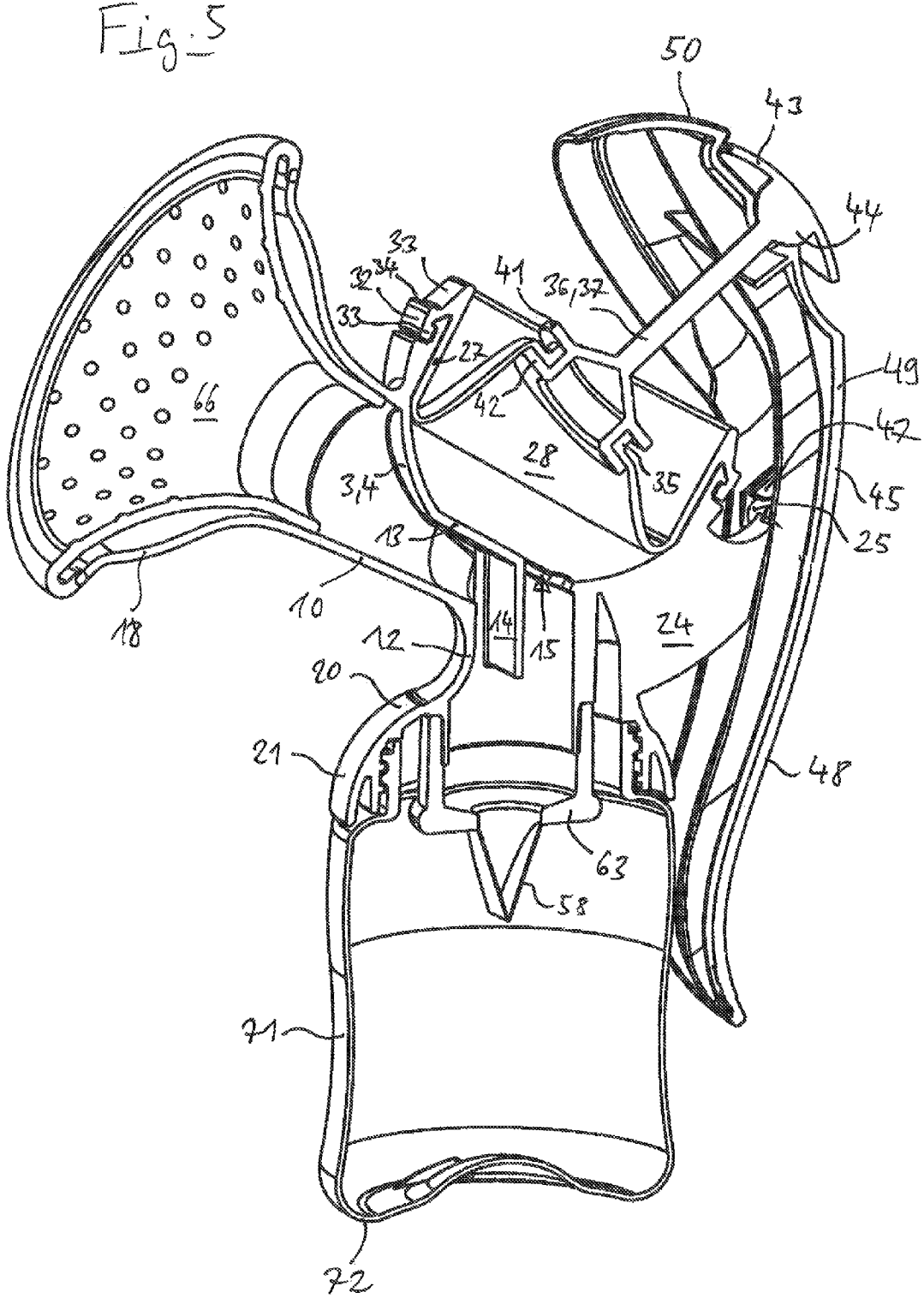

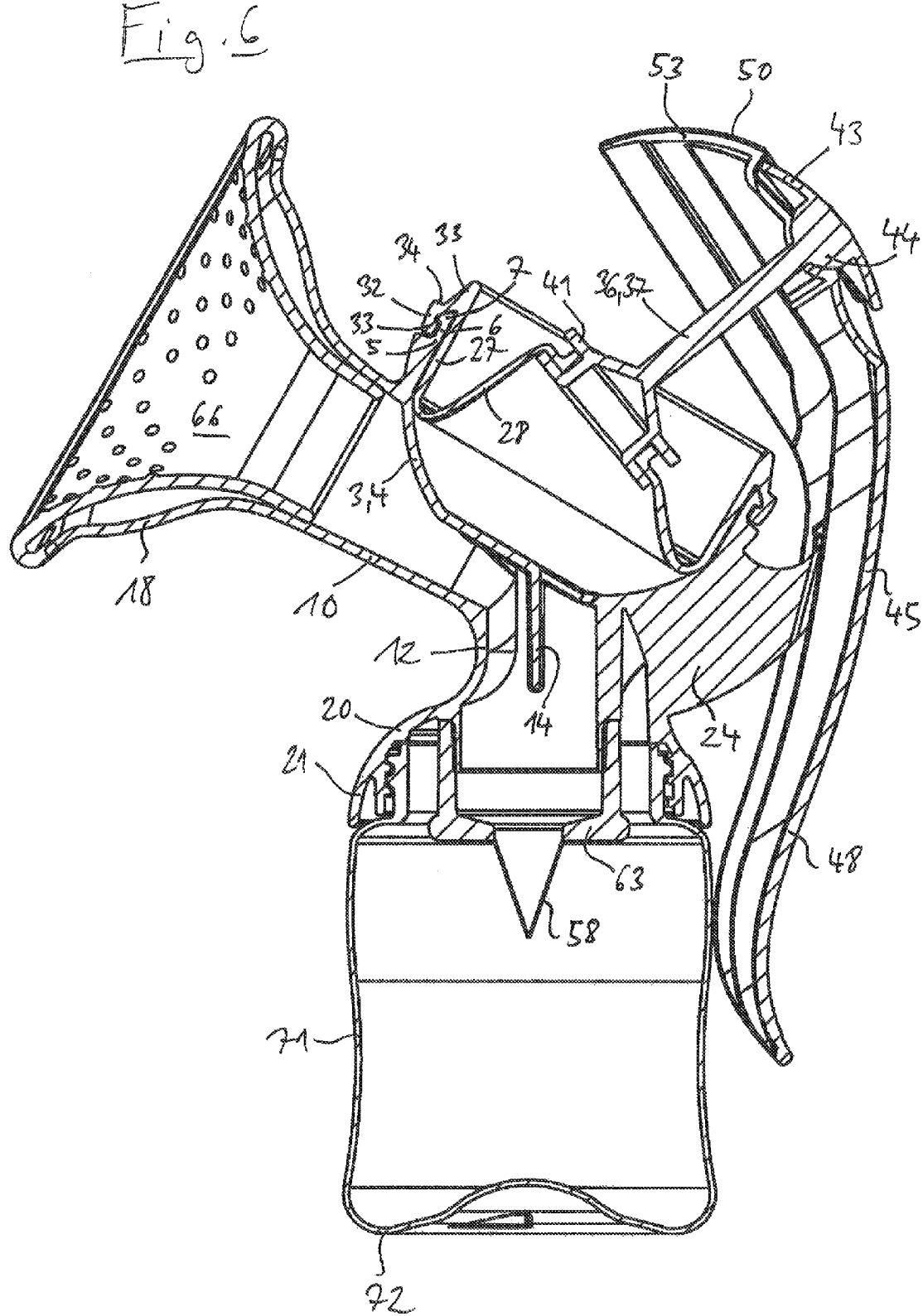

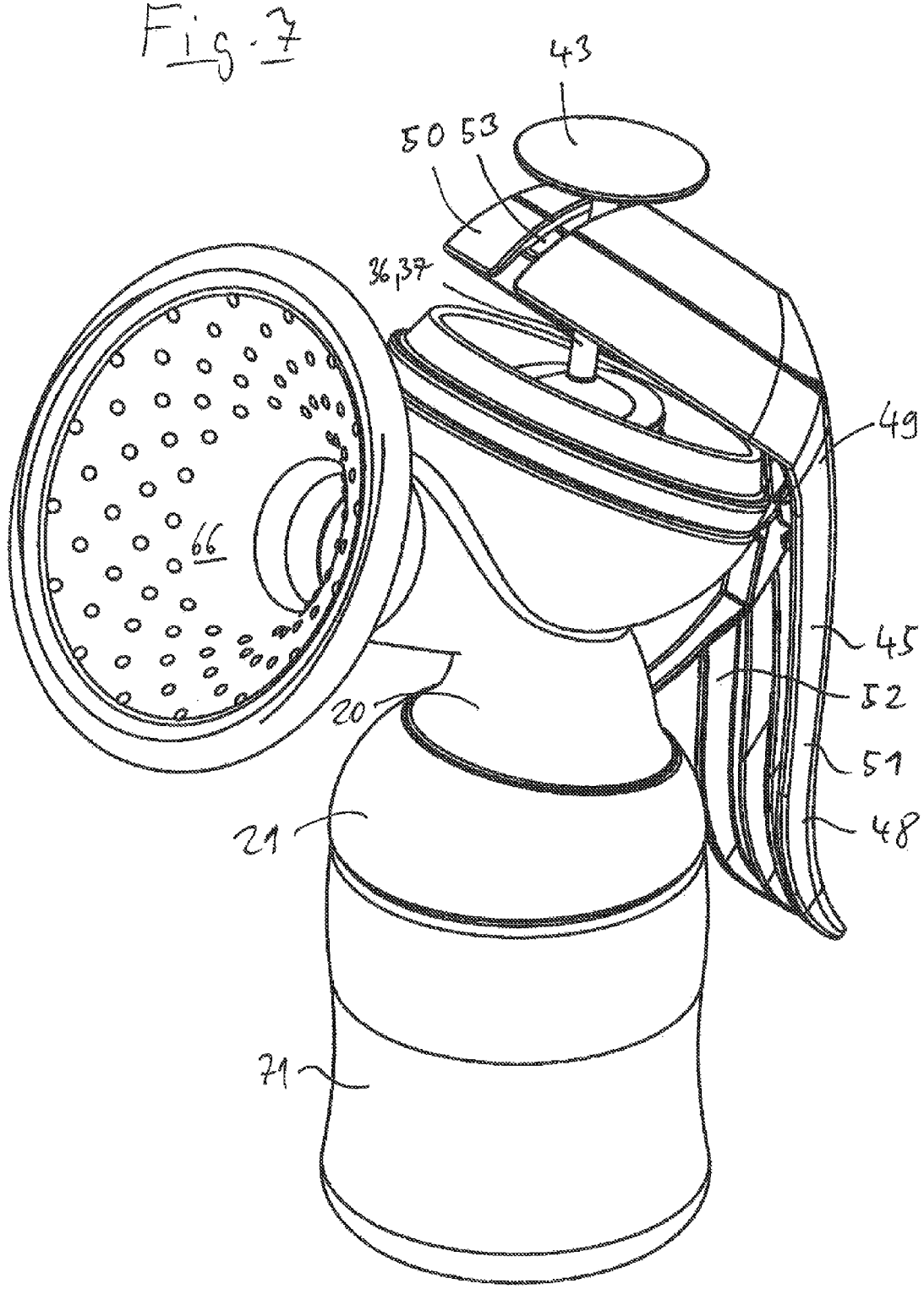

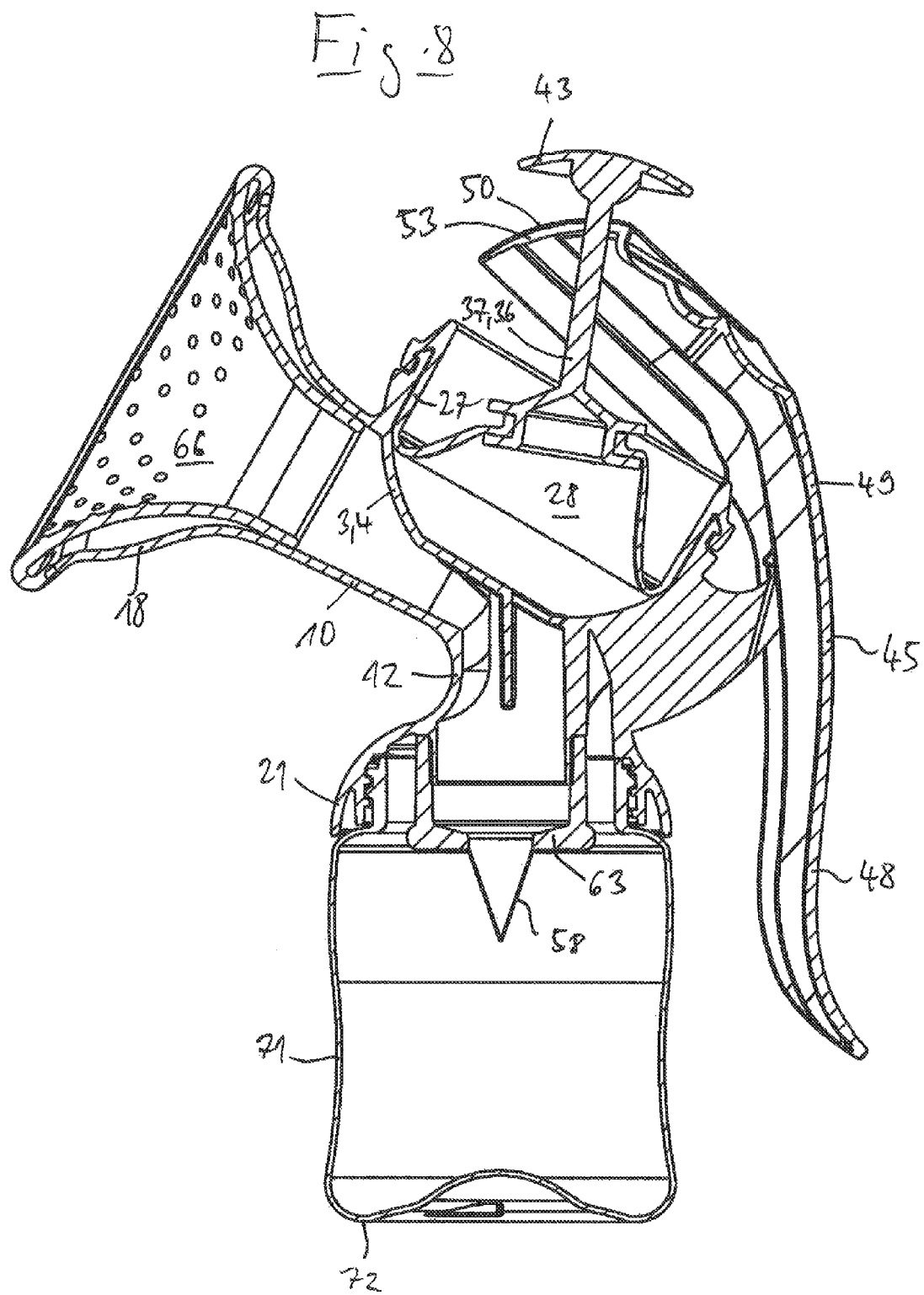

MANUAL BREAST PUMP

CROSS-REFERENCE TO RELATED APPLICATIONS

This application claims priority to DE 20 2012 008 803.3, filed on Sep. 14, 2012

STATEMENT REGARDING FEDERALLY SPONSORED RESEARCH

Not applicable.

BACKGROUND OF THE INVENTION

The invention relates to a manual breast milk pump.

Breast milk pumps serve to pump breast milk. For this, they have at least one suction bell, which is put on the mother's breast. Negative pressure is supplied to the suction bell in order to draw milk from the breast. The suction bell is connected with a milk collection container, which receives the suctioned breast milk. The negative pressure is repeatedly supplied to and relieved from the suction bell in order to stimulate the flow of milk. The negative pressure is generated by means of a pump, which is actuated manually in the case of a manual breast milk pump. In the case of an electric breast milk pump, the pump is actuated by means of an electric motor.

For example, breast milk pumps in which the pumps have a cylinder with a piston that is displaceable in it, which is actuatable by means of a lever, are known e.g. from EP 1 231 955 B1, the entire contents of which are incorporated herein by reference. The disadvantage of such pumps is the complex construction and the considerable cleaning effort. Pumping is tiring, in particular because the friction resistance between the piston and cylinder must be overcome.

Furthermore, breast milk pumps are known e.g. from EP 1 515 760 B1, the entire contents of which are incorporated herein by reference, in which the suction bell is connected with a displacement chamber, which is sealed closed by a membrane. The membrane is deflectable by means of a lever, in order to produce negative pressure in the displacement chamber. By returning the membrane to its original position, the negative pressure is relieved. The suction bell is connected with a milk collection container via an outlet valve. The outlet valve closes when there is negative pressure in the displacement chamber so that the milk collects in front of the valve. When the negative pressure is relieved, the outlet valve opens and the milk drains into the milk collection container. Pump work is spared through the outlet valve since the negative pressure is only reached in the suction bell and in the displacement chamber and not in the milk collection container. The disassembly of the breast milk pump for cleaning purposes and the subsequent reassembly of the pump is complicated.

Against this background, the object of the invention is to create a manual breast milk pump, which can be disassembled and reassembled with less effort in particular for the purpose of cleaning.

BRIEF SUMMARY OF THE INVENTION

The manual breast milk pump according to the invention comprises
a housing, which
has a cup-like displacement chamber,
has a connection channel, which has an inlet opening on the top and an outlet opening on the bottom, and is connected in a communicating manner with a bottom part of the displacement chamber between the inlet opening and the outlet opening and
has means for the releasable connection of the housing with an opening edge of a milk collection container upon alignment of the outlet opening with opening of the milk collection container,
a milk collection container connected with the means for releasable connection,
a suction bell, which is designed to receive a part of a breast and is connected with the inlet opening of the connection channel,
a cup-like membrane element made of an elastomer material, which has on its upper edge first means for releasable and sealing connection, which are connected in a releasable and sealing manner with an upper edge of the displacement chamber,
a coupling element, which has a coupling rod, which is connected on the bottom with a bottom of the membrane element, and said coupling element being connected with the upper end of the coupling rod and protruding laterally over the coupling rod,
a lever with a first lever arm and a second lever arm, wherein the second lever arm comprises a cover placeable on the upper edge of the membrane element,
means for the rotatable mounting of the lever, which mount the lever rotatably between the first lever arm and the second lever arm on the housing, wherein in the lever's idle position the first lever arm is arranged laterally at a distance from the housing and the second lever arm is arranged with the cover on the upper edge of the membrane element so that the lever through rotation of the first lever arm towards the housing is rotatable with the second lever arm away from the displacement chamber and the coupling element bulges out a part of the membrane element, which is arranged within the upper edge of the membrane element and
an insertion slot, which extends on the free end of the second lever arm up to a distance from the means for rotatable mounting and reaches from the outside up to the inside of the second lever arm, wherein the coupling rod reaches through the insertion slot and the head of the coupling element above the insertion slot is supported on the outside of the cover.

In the case of the manual breast pump according to the invention, the coupling element is installed with a coupling rod into the insertion slot and is supported with the head on the outside of the cover. This enables a particularly simple release of the coupling element from the lever through rotation of the coupling rod through the insertion slot and beyond the free end of the second lever arm. The connection between the membrane element and the displacement chamber does not hereby need to be released because the elasticity of the membrane element permits a rotation of the coupling element. Conversely, the coupling element with the coupling rod can be easily inserted into the insertion slot from the free end of the second lever arm. Moreover, the membrane element is connected on its upper edge with the upper edge of the displacement chamber in a releasable and sealing manner via the first means for releasable and sealing connection. After the coupling element is rotated out of the insertion slot, this connection between the membrane element and the displacement chamber is easily releasable. After the release of the connection, the membrane element can be removed from the displacement chamber. It is hereby advantageous that the lever can be rotated away after rotating the coupling element out of the insertion slot with the cover of the displacement chamber so that the displacement chamber is easily accessible from the outside for removal of the membrane element with the coupling element connected with it. Conversely, the membrane element with the coupling element connected with it can be easily inserted into the displacement chamber and is combinable on its upper edge in a sealing manner with the upper edge of the displacement chamber if the lever is rotated away with the cover of the displacement chamber. The breast milk pump can be easily disassembled into individual parts for the purpose of cleaning or for the purpose of replacing the membrane element. The parts of the breast milk pump can then be subjected to a particularly thorough cleaning. Due to the membrane element, the breast milk pump has the advantage that it enables pumping with relatively little effort. During the outward bulging, the membrane is stretched elastically. As a result, the membrane element automatically returns to its initial shape after release of the lever and hereby rotates the lever into the idle position.

According to one embodiment, the breast milk pump has an outlet valve held sealed on the outlet opening via second means for releasable and sealing connection that closes when the difference in the pressure in the milk collection container and in the connection channel has a certain minimum value and that opens when the minimum value is fallen short of. The pumping effort required is further reduced by the outlet valve because negative pressure is not created in the milk collection container.

According to one embodiment of the invention, the suction bell is connected with the housing as one piece so that the suction bell and housing form one stable unit. For cleaning purposes, it is not necessary to separate the suction bell from the housing.

According to a further embodiment, the suction bell bulges outward between its large opening and its small opening. The contouring of the suction bell is advantageous for the fit on the breast. According to a further embodiment, a funnel-shaped insert made of soft elastic material is inserted into the suction bell, which is connected on its large funnel opening via third means for releasable and sealing connection with the edge of the large opening of the suction bell. The insert made of soft elastic material fits the shape of the breast and pads the suction bell. An air cushion forms between the suction bell and the insert when the suction bell bulges outward between its large and its small opening so that the insert rests particularly softly on the breast.

According to a further embodiment, the funnel-shaped insert has its small funnel opening in a neck, which rests with its outer circumference sealingly on the inner circumference of the inlet opening. As a result, when vacuum is supplied, air cushions cannot escape between the insert and the suction bell so that the insert rests particularly softly on the breast.

According to a further embodiment, the connection channel has the inlet opening on a diagonally upward sloping upper channel section and the outlet opening on a vertically downward pointing lower channel section. This embodiment of the connection channel is advantageous for using the breast milk pump in a seated position. The suction bell can placed on the breast sloping slightly upwards; the milk drains through the upper channel section and collects in the lower channel section above the outlet valve, through which it drains into the milk collection container. According to a preferred embodiment, the upper channel section is designed in an upper tube socket and the lower channel section in a lower tube socket of the housing.

According to a further embodiment, the centre axis of the cup-like displacement chamber is aligned at an acute angle to the vertical line on the side facing away from the suction bell. Furthermore, the centre axis of the cup-like displacement chamber is preferably perpendicular on the longitudinal axis of the upper channel section. This is advantageous for a space-saving arrangement of the displacement chamber and a large displacement volume of the membrane.

According to a further embodiment, the first means for releasable and sealing connection has a circumferential collar fold on the upper edge of the membrane element, into which a circumferential shoulder on the upper edge of the displacement chamber engages, wherein the collar fold and the shoulder have circumferential hook profiles engaging behind each other. This embodiment is advantageous for a secure fixing of the membrane element on the displacement chamber, which does not release when the membrane element bulges upward. However, the releasable connection is easily releasable on purpose for disassembling the breast milk pump in that the collar fold is raised at one location and the upper edge of the membrane element is pulled from the shoulder of the displacement chamber. Conversely, the membrane element is easily mountable on the displacement chamber through positioning of the collar fold on the shoulder and pressing onto the shoulder until the hook profiles engage behind each other.

According to a further embodiment, the membrane element has a circumferential lip protruding upwards from its upper edge, on which the cover sits when the lever is in idle position. The lip dampens the impact of the lever when the idle position is reached. Furthermore, it seals the cover on the lower edge in idle position and prevents the deposit of impurities on the top side of the membrane element. Moreover, the lip holds the cover in a predetermined alignment and thus protects the means for the mounting of the lever, for example if the pump falls over.

According to a further embodiment, the membrane element has a circumferential step on the upper edge, on which the cover sits when the lever is in idle position. The step dampens the impact of the lever when the idle position is reached.

According to a further embodiment, a housing part containing the displacement chamber is spherical-segment-shaped and the cover is also spherical-segment-shaped and the spherical-segment-shaped housing part and the spherical-segment-shaped cover in the idle state of the lever mainly have the shape of a hollow sphere. The sphere shape has a pleasant surface feel. Moreover, the free space between the cover and the displacement chamber is particularly large when the first lever arm is rotated towards the housing, whereby removal and insertion of the membrane element is facilitated.

According to a further embodiment, the coupling rod has two discs with a circumferential annular gap in between on its lower end and the cup-like membrane element is held on the edge of a hole in its bottom between the discs. This embodiment favours a simple separation of the coupling element from the membrane element and connection of the coupling element with the membrane element, for example for the purposes of cleaning and replacement. Alternatively, the membrane element is permanently connected with the coupling element. The invention includes potential embodiments in which the coupling element is connected with the membrane element as one piece. In particular, the invention relates to possible embodiments, in which the coupling element is made of the same material as the membrane element.

According to one embodiment, the head of the coupling element is supported laterally at least on the sides pointing towards the free end of the second lever arm with a protrusion on the outside of the cover. The head is hereby prevented from accidentally sliding out of the insertion slot. In the opposite direction, the coupling element is preferably supported by attachment of the coupling rod on the inner end of the insertion slot. According to a preferred embodiment, the head of the coupling element is inserted into a recess on the outside of the cover. In this embodiment, the edge of the recess forms the protrusion, which supports the head in the direction of the free end of the second lever arm.

According to a further embodiment, the head has the shape of a spherical cap on the outside and has together with the spherical-segment-shaped cover and the spherical-segment-shaped housing part in the idle state of the lever mainly the shape of a sphere. In this embodiment, the head complements the sphere formed by the housing part and the cover.

According to a further embodiment, the cover has a trough next to the supporting area of the head, into which a fingertip can be inserted in order to lift the head out of the recess. This facilitates the disassembly of the breast milk pump.

According to a further embodiment, the outlet valve is a duckbill valve. The duckbill valve is simple, fail-safe and easy to clean. In terms of easy cleaning, the discharge valve is preferably held on the lower end of a lower tube socket having the outlet opening. The outlet valve is preferably held on the lower tube socket by a clamp connection. If the outlet valve is a duckbill valve, it preferably has a pot-like holder, pushed onto or into the lower tube socket under light elastic deformation.

According to a further embodiment, the cup-like membrane element and/or the soft elastic insert and/or the duckbill valve is made of a silicone elastomer. The lever and the housing as well as the suction bell are made of a mainly rigid plastic according to a preferred embodiment.

BRIEF DESCRIPTION OF THE SEVERAL VIEWS OF THE DRAWINGS

The invention is explained in greater detail below based on included drawings of an exemplary embodiment. The drawings show:

FIG. 4 the breast milk pump with actuated lever in a perspective view diagonally from the front and from the side;

FIG. 5 the breast milk pump with actuated lever in a vertical cut in the same perspective view;

FIG. 6 the breast milk pump with actuated lever in a vertical cut;

FIG. 7 the breast milk pump during feeding of the coupling rod through the insertion slot in a perspective view diagonally from the front and from the side;

FIG. 8 the breast milk pump during feeding of the coupling rod through the insertion slot in a vertical cut.

DETAILED DESCRIPTION OF THE INVENTION

Figure 1:
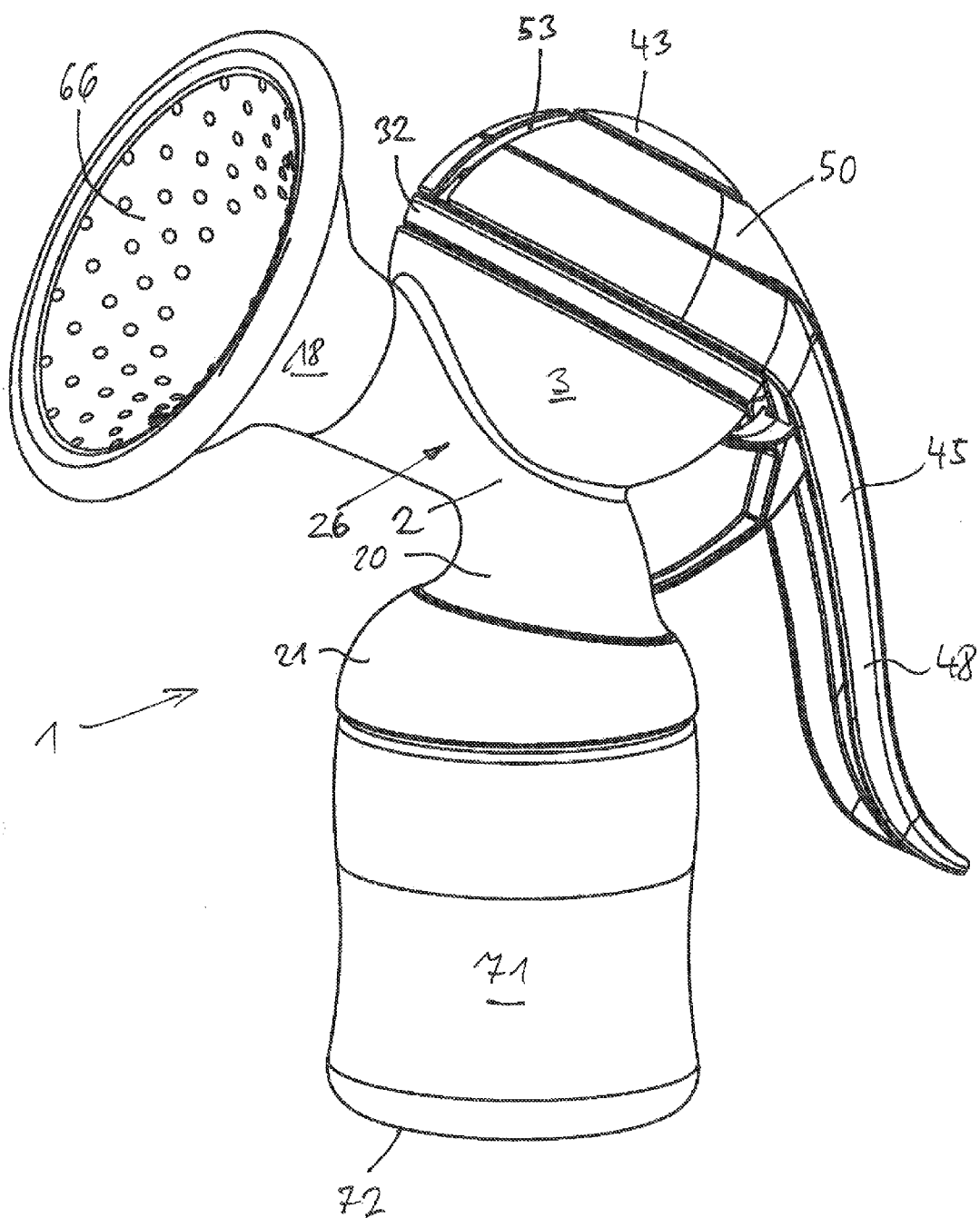
FIG. 1 a manual breast milk pump in the idle state of the lever in a perspective view diagonally from the front and from the side.

While this invention may be embodied in many different forms, there are described in detail herein a specific preferred embodiment of the invention. This description is an exemplification of the principles of the invention and is not intended to limit the invention to the particular embodiment illustrated In the present application, the terms "upper" and "lower" refer to an arrangement, in which the breast milk pump with a base of the milk collection container, which is arranged on the end of the milk collection container opposite of the opening edge, sits on a horizontal surface.

The breast milk pump 1 has a housing 2, which has a cup-like displacement chamber 3. The displacement chamber 3 has a mainly spherical-segment shape on the outside and in the lower part 4 on the inside. In the example, it is the shape of a hemisphere. In an upper part, the displacement chamber 3 is cylindrical inside. On the upper edge 5, the displacement chamber 3 has a protruding, circumferential shoulder 6, which has a circumferential hook profile 7 on the outside.

Furthermore, the housing 2 has a connection channel 8. The connection channel 8 has an upper channel section 9, which is arranged in an upper tube socket 10 sloped upwards at an acute angle. On the bottom, the connection channel 8 has a lower channel section 11, which is arranged in a vertical, lower tube socket 12. The upper tube socket 10 and the lower tube socket 12 are interconnected.

The displacement chamber 3 is aligned with its centre axis perpendicular to the longitudinal axis of the upper tube socket 10. With its chamber floor 13 and its lower part 4, in which it is spherical inside and outside, it engages in the upper area of the tube socket 10.

From the chamber floor 13 of the displacement chamber 3, a splashback 14 extends downward into the lower tube socket 12 and divides the lower tube socket 12 in the upper area in the centre into two separate chambers. Next to the splashback 14, the displacement chamber 3 has a through hole 15 to the lower tube socket 12.

The upper tube socket 10 has an inlet opening 16 of the connection channel 8 on the top and the lower tube socket 12 has an outlet opening 17 of the connection channel 8 on the bottom.

The upper tube socket 10 is connected as one piece with a small opening of a suction bell 18 at the inlet opening 16. The suction bell 18 bulges outwards circumferentially between its large opening 19 and its small opening.

The housing 2 has a circumferential casing 20 below the displacement chamber 3, which extends downwards gradually. In its upper part, the casing 20 on the side of the upper tube socket 10 is simultaneously the casing of the lower tube socket 12, i.e. the walls of the casing 20 and of the lower tube socket 12 come together in this area. On the opposite side of the lower tube socket 12, the casing 20 is separated from the lower tube socket 12. This area begins approximately at the diametrically opposed locations, at which the splashback 14 is connected with the lower tube socket 12 on both sides. In its lower part, the casing 20 extends towards a hood 21 circumferentially. A lower part of the lower tube socket 12 protrudes into the hood 21. On the bottom, a cylindrical shell 22 with an internal thread 23 for screwing onto an outer thread of a milk collection container protrudes from the inside of the hood 21.

On the side of the displacement chamber 3, which is arranged diametrically opposed to the upper tube socket 10, the housing 2 has a rib-shaped support 24 with a horizontal bearing axis 25 on the upper end, which is aligned perpendicular to the longitudinal axis of the upper tube socket 10 and the suction bell 18.

The protruding elements of the housing 2 and the suction bell 18 are permanently interconnected to form a uniform pump top part 26. The housing 2 with the suction bell 18 is preferably made of a hard plastic, in particular through injection moulding. The parts of the pump top part 26 can be prefabricated separately and then permanently connected with each other, for example through heat sealing.

Furthermore, the breast milk pump 1 comprises a cup-like membrane element 27 made of an elastomer material. The membrane element 27 has a base 28 with a central hole 29. Starting from the edge of the base 28, the membrane element 27 has a hemispherical-segment-shaped membrane section 30 and a hollow cylindrical membrane section 31 adjacent to it. In this respect, the outer shape of the membrane element 27 is adapted to the inner shape of the displacement chamber 3.

On the upper edge 31, the membrane element 27 has a collar fold 32 on the outside. In the collar fold 32, the membrane element 27 has a circumferential hook profile (shown generally at 33), which is shaped complementary to the hook profile 7 and is hooked with it.

On the upper edge 31, the membrane element 27 has a protruding, circumferential upper lip 33. Furthermore, the membrane element 27 has a circumferential step 34 on the upper edge 31 outside of the lip 33.

Adjacent to the hole 29, the membrane element 27 has a circumferential, upwards protruding lower lip 35.

The membrane element 27 is manufactured as a single part from a silicone elastomer.

Furthermore, the breast milk pump 1 comprises a coupling element 36. The coupling element 36 has a coupling rod 37, which has a connection element for connection with the membrane element 27 on the bottom. The connection element comprises a hollow cylindrical section 39, which is connected with the coupling rod 37 via a conical section 40. Two spaced discs 41, 42 protrude from the circumference of the hollow cylindrical section 39. The base 28 of the membrane element 27 is held at the end of the hole 29 in the distance area between the discs 41, 42 so that the lower lip 35 rests against the casing of the hollow cylindrical section 39 and against the discs 41, 42.

Furthermore, the coupling element 36 comprises a head 43, which is connected with the upper end of the coupling rod 37. The head 43 has the shape of a spherical cap. The connection of the head 43 with the coupling rod 37 is reinforced via several stiffening ribs 44, which protrude radially from the coupling rod 37 and are connected with the bottom side of the head 43. On the lower edge, the stiffening ribs 44 have a concordant radius, so that they are rotatable in a spherical shell.

The coupling element 36 is manufactured as a single part from a hard plastic, preferably through injection moulding.

Furthermore, the breast milk pump 1 comprises a lever 45 with parallel bearing lugs 46, 47 between a first lever arm 48 and a second lever arm 49. The bearing lugs 46, 47 are eyelet-shaped and clamped on the bearing axis 25 of the housing 2.

The first lever arm 48 is designed as a handle with an outwardly bent lower end, which should prevent a hand from slipping off. The second lever arm 49 is widened into a cover 50 at a short distance from the bearing lugs 46, 47. In the area of the cover 50, the lever is spherical-segment-shaped and bulges outward in the remaining areas. Furthermore, the lever 45 has on both edges side walls 51, 52 protruding from one side, which transition on the top into the edges of the cover 50. Overall, the transition from the cover 50 to the other parts of the lever 45 is smooth on the outside.

Furthermore, the lever 45 has an insertion slot 53, which comes from the free end of the second lever arm 49. The insertion slot 53 extends up to the crest or respectively pole of the spherical-segment-shaped cover 50. On the end of the insertion slot 53, a spherical-shell-shaped recess 54 is present on the outside of the cover 50, against which the stiffening ribs 44 rest with their bottom side. Furthermore, the outside of the cover has a recess 55 that is concentric with respect to the recess described above, which mainly receives the head 43 of the coupling element 36. Moreover, the cover 50 has a trough 56 facing away from the insertion slot 53, which is arranged in part next to the last-mentioned recess 55 and in part engages in this recess 55 so that a fingertip inserted into the trough 56 can engage under the head 43 of the coupling element 35 in the recess 55.

Figure 2:
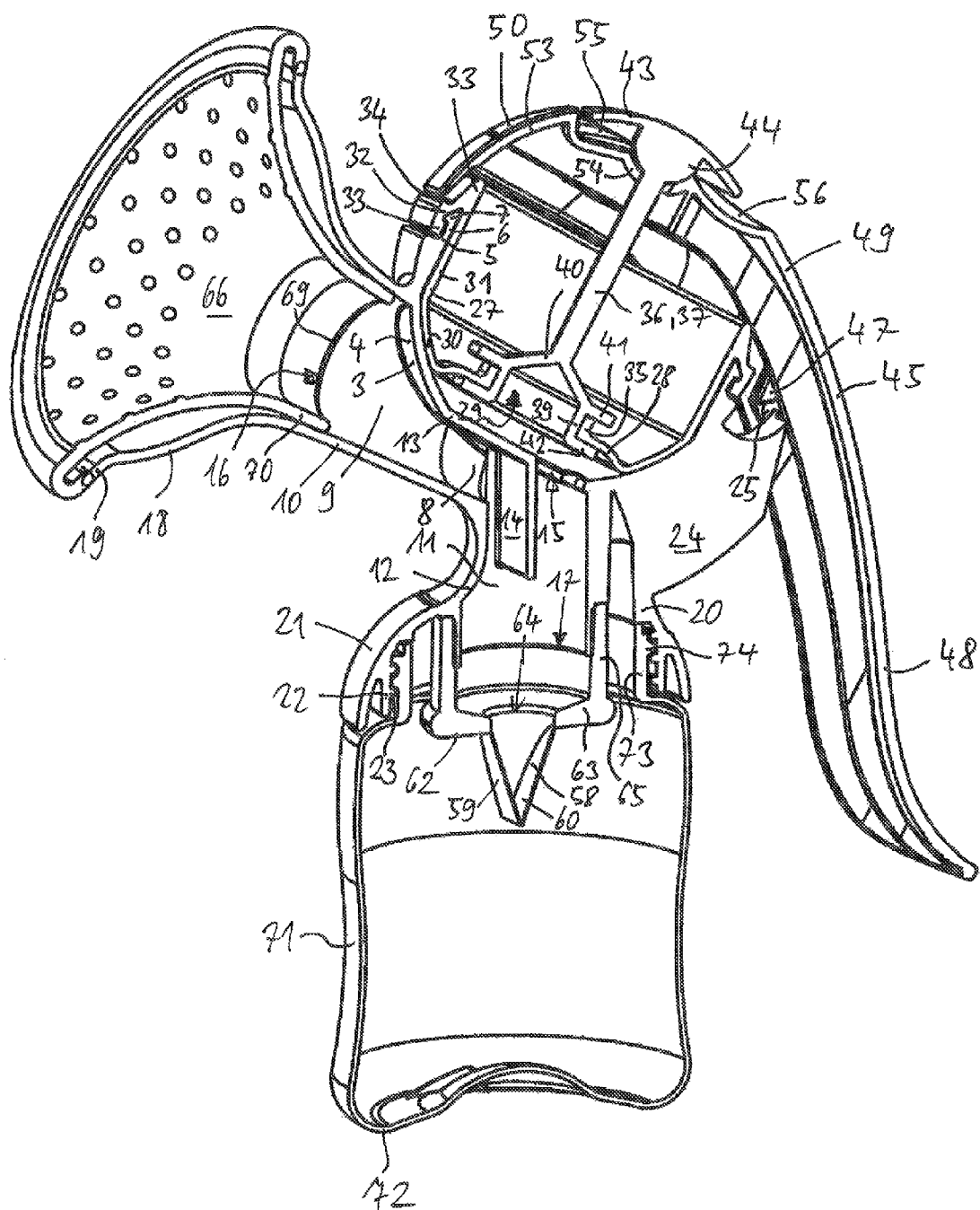
FIG. 2 the breast milk pump in the idle state of the lever vertically cut in the same perspective view.

The lever 45 is clamped onto the bearing axis 25 with the bearing lugs 46, 47. The coupling element 36 holds the lever 45 in the idle position from FIGS. 1 and 2, in which the cover 50 with the lower edge sits on the step 34 of the membrane element 27 and rests against the upper lip 33.

The lever 45 is made of a hard plastic. It is preferably injection-moulded from the plastic.

Furthermore, the breast milk pump 1 comprises an outlet valve 58, which is designed as a duckbill valve. The duckbill valve is a tube piece, which has two flat side walls 59, 60, which lean towards each other and touch each other on the bottom along a sealing line. The duckbill valve is made of an elastomer, preferably a silicone elastomer.

The outlet valve 58 protrudes from the bottom side of the bottom 62 of a pot-like holder 63, wherein the bottom 62 has a hole 64 in the area of the outlet valve 58. The outlet valve 58 is preferably manufactured as a single part with the holder 63. The holder and duckbill valve preferably consist of the same elastomer, in particular a silicone elastomer.

The outlet valve 58 is clamped with a cylindrical casing part 65 of the holder 63 in a sealing manner on the lower end of the lower tube socket 12.

Furthermore, the breast milk pump 1 comprises a funnel-shaped insert 66 made of an elastomer material. The insert 66 has a fold folded back and outwards at its large opening. With this fold, the insert 66 is clamped onto the edge of the large opening 19 of the suction bell 18.

The insert 66 has its small opening 69 in a neck 70, which rests on the outer circumference in a sealing manner against the upper tube socket 10.

A circumferential air cushion is present between the insert 66 and the suction bell 18.

The insert 66 is preferably manufactured as a single part from an elastomer material, in particular from a silicone elastomer.

Finally, the breast milk pump 1 comprises a milk collection container 71. The milk collection container 71 has a bottle shape. On the bottom, it has a base 72 and on the top a neck 73 with an external thread 74. The housing 2 is screwed onto the external thread 74 with the internal thread 23. The milk collection container 71 can also be used as a feeding bottle after being filled with milk.

The milk collection container 71 is preferably made of a rigid plastic. It is preferably injection-moulded as a single part from the plastic.

For pumping of milk, the breast milk pump 1 with the suction bell 18 is placed on a breast so that it rests on the outside of the insert 66. The lever 45 is then cyclically actuated in that the first lever arm 48 is pressed in the direction of the housing 7 or respectively the milk collection container 71 and then released.

Figure 3:
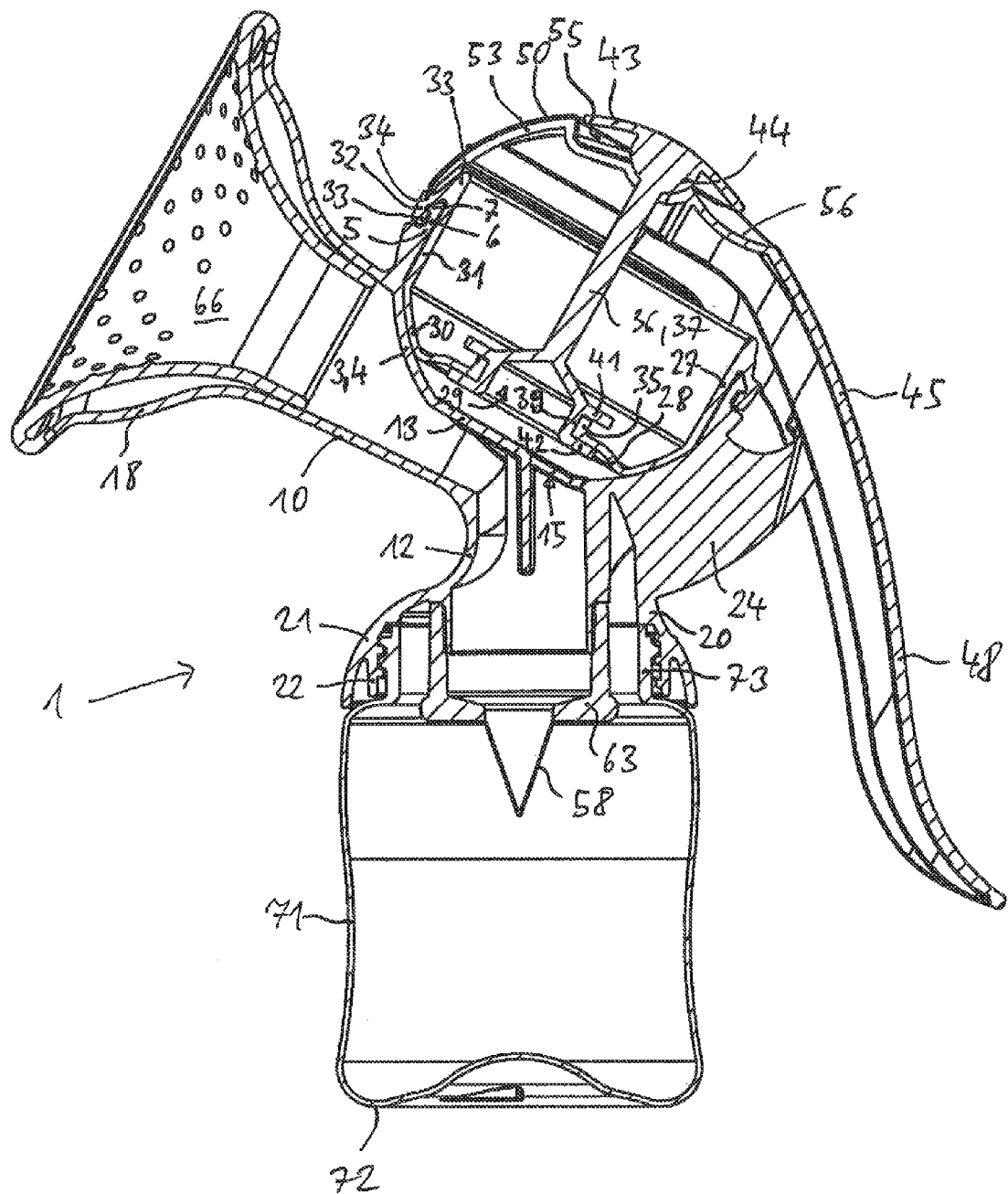
FIG. 3 the breast milk pump in the idle state of the lever in a vertical cut.

By actuating the lever 45, the membrane element 27 is deflected upwards as shown in FIGS. 4, 5, 6. Negative pressure is hereby generated in the displacement chamber 3 and in the suction bell 18. After the lever 45 is released, the membrane element 27 takes on its initial shape and pulls the lever 45 back into the idle position in FIGS. 1, 2, 3. The negative pressure is hereby reduced again in the displacement chamber 3 and in the suction bell 18.

The milk flow is stimulated through cyclical generation and reduction of the negative pressure. The milk drains off through the insert 66 and the connection channel 8 into the duckbill valve 58. If there is negative pressure in the displacement chamber 3 and thus in the connection channel 8, the duckbill valve 58 closes and holds the milk tight. When the negative pressure is relieved, the duckbill valve 58 opens and releases the milk into the milk collection container 71.

After the milk has been pumped, the housing 2 is screwed off the milk collection container 71 and the milk collection container 71 is closed for the purpose of preserving the milk or is provided with a bottle teat to dispense the milk.

The housing 2 is screwed off the milk collection container 71 for the cleaning of the breast milk pump 1. Furthermore, the coupling element 36 is released from the lever 45 in that the head 43 is rotated out of the insertion slot 53 with the fingertip, as shown in FIGS. 7, 8. The membrane element 27 is then releasable from the housing 2 by being forced off the shoulder 6.

The duckbill valve 58 can be separated from the housing 3 by being forced off the lower tube socket 12.

The insert 66 is releasable by being forced off the upper edge of the suction bell 18.

The lever 45 can be separated from the bearing axis 25 of the housing 2 by being forced off the bearing lugs 46, 47.

The milk collection container 71 is releasable by being screwed off the housing 2.

The aforementioned individual parts can be cleaned and, if necessary, sterilized individually. They can then be easily reassembled in the reverse order.

This completes the description of the preferred and alternate embodiments of the invention. Those skilled in the art may recognize other equivalents to the specific embodiment described herein which equivalents are intended to be encompassed by the claims attached hereto.

What is claimed is:

1. Manual breast milk pump comprising
   a housing (2), which
      has a cup-like displacement chamber (3),
      has a connection channel (8), which has an inlet opening (16) on the top and an outlet opening (17) on the bottom, and is connected in a communicating manner with a bottom part of the displacement chamber (3) between the inlet opening (16) and the outlet opening (17) and
      has means for a releasable connection (23) of the housing (2) with an opening edge (73) of a milk collection container (71),
   the milk collection container (71) connected with the means for releasable connection (23),
   a suction bell (18), which is designed to receive a part of a breast and is connected with the inlet opening (16) of the connection channel (8),
   a cup-like membrane element (27) made of an elastomer material, which has on its upper edge (31) first means for releasable and sealing connection (32, 33), which are connected in a releasable and sealing manner with an upper edge of the displacement chamber (3),
   a coupling element (36), which has a coupling rod (37), which is connected on the bottom to a bottom (28) of the cup-like membrane element (27), and said coupling element having a spherical head (43), which is connected with the upper end (37) of the coupling rod and protrudes laterally over the coupling rod (37),
   a lever (45) with a first lever arm (48) and second lever arm (49), wherein the second lever arm (49) comprises a cylindrical-segment-shaped cover (50) placeable on the upper edge of the membrane element (27),
   means for the rotatable mounting (25, 46, 47) of the lever (45), which mount the lever (45) rotatably between the first lever arm (48) and the second lever arm (49) on the housing (2), wherein in the lever's idle position (49) the first lever arm (48) is arranged laterally at a distance from the housing (2) and the second lever arm (49) is arranged with the cover (50) on the upper edge of the membrane element (27) so that the lever (45) through rotation of the first lever arm (48) towards the housing (2) is rotatable with the second lever arm (49) away from the displacement chamber (3) and thereby bulges a part of the membrane element (27) within its upper edge (31) upwards via the coupling element (36), and
   an insertion slot (53), which reaches from the outside up to the inside of the second lever arm (49) and extends from the free end of the second lever arm (49) up to a distance from the means for rotatable mounting (25, 46, 47), wherein the coupling rod (37) reaches through the insertion slot (53) and the spherical head (43) of the coupling element (36) above the insertion slot (53) is supported on the outside of the cover (50), wherein
   the insertion slot (53) extends up to the crest of the cylindrical-segment-shaped cover (50),
   a spherical-shell-shaped recess is formed on the outside of the cover (50),
   stiffening ribs (44) of the spherical head (43) engage the recess,
   the outer side of the cover (50) has a recess (55) concentric with respect to the spherical-shell-shaped recess (54) which accommodates the head (43) of the coupling element (36),
   the cover (50) has a trough (56) facing away from the insertion slot (53), which is arranged in part next to the recess (55) and in part engages in this recess (55) so that a fingertip inserted into the trough (56) can engage under the head (43) in the recess (55).

2. The breast milk pump according to claim 1, comprising an outlet valve (58) held sealed on the outlet opening (17) via a second means for releasable and sealing connection (63) that closes when the difference in the pressure in the milk collection container (71) and in the connection channel (8) has a certain minimum value and that opens when the minimum value is fallen short of.

3. The breast milk pump according to claim 1, in which the suction bell (18) is connected with the housing (2) as one single part.

4. The breast milk pump according to claim 1, in which the suction bell (18) bulges outward between its large opening and its small opening.

5. The breast milk pump according to claim 1, in which a funnel-shaped insert (66) made of soft elastic material is inserted into the suction bell (18), said funnel-shaped insert being connected on its large funnel opening via third means for releasable and sealing connection with the edge of the large opening of the suction bell (18).

6. The breast milk pump according to claim 5, in which the funnel-shaped insert (66) has its small opening (69) in a neck (70), which rests with its outer circumference in a sealing manner on the inner circumference of the inlet opening (16).

7. The breast milk pump according to claim 1, in which the connection channel (8) has the inlet opening (16) on a diagonally upward sloping upper channel section (9) and the outlet opening on a vertically downward pointing lower channel section (10).

8. The breast milk pump according to claim 1, in which the centre axis of the cup-like displacement chamber (3) is aligned at an acute angle to the vertical line on the side facing away from the suction bell (18).

9. The breast milk pump according to claim 1, in which the first means for releasable and sealing connection has a circumferential collar fold (32) on the upper edge of the membrane element (27), into which a circumferential shoulder (6) on the upper edge of the displacement chamber (3) engages, wherein the collar fold (32) and the shoulder (6) have circumferential hook profiles (7, 33) engaging behind each other.

10. The breast milk pump according to claim 1, in which the membrane element (27) has a circumferential upper lip (33) protruding upwards from its upper edge, on which the cover (50) sits in the idle position of the lever (45).

11. The breast milk pump according to claim 1, in which the membrane element (27) has a circumferential step (34) on the upper edge, on which the cover (50) sits in the idle position of the lever (45).

12. The breast milk pump according to claim 1, in which a housing part containing the displacement chamber (3) is spherical-segment-shaped and the cover (50) is also spherical-segment-shaped and the spherical-segment-shaped housing part and the spherical-segment-shaped cover (50) have together in the idle state of the lever (45) mainly the shape of a hollow sphere.

13. The breast milk pump according to claim 1, in which the coupling rod (37) has two discs (41, 42) with a circumferential annular gap in between on the lower end and the cup-like membrane element (27) is held on the edge of a hole (29) in its bottom (28) between the discs (41, 42).

14. The breast milk pump according to claim 1, in which the head (43) of the coupling element (36) is inserted into the recess (55) on the outside of the cover (50).

15. Manual breast milk pump comprising
 a housing (2), which
  has a cup-like displacement chamber (3),
  has a connection channel (8), which has an inlet opening (16) on the top and an outlet opening (17) on the bottom, and is connected in a communicating manner with a bottom part of the displacement chamber (3) between the inlet opening (16) and the outlet opening (17) and
  has means for a releasable connection (23) of the housing (2) with an opening edge (73) of a milk collection container (71),
 the milk collection container (71) connected with the means for releasable connection (23),
 a suction bell (18), which is designed to receive a part of a breast and is connected with the inlet opening (16) of the connection channel (8),
 a cup-like membrane element (27) made of an elastomer material, which has on its upper edge (31) first means for releasable and sealing connection (32, 33), which are connected in a releasable and sealing manner with an upper edge of the displacement chamber (3),
 a coupling element (36), which has a coupling rod (37), which is connected on the bottom to a bottom (28) of the cup-like membrane element (27), and said coupling element having a head (43), which is connected with the upper end (37) of the coupling rod and protrudes laterally over the coupling rod (37),
 a lever (45) with a first lever arm (48) and second lever arm (49), wherein the second lever arm (49) comprises a cover (50) placeable on the upper edge of the membrane element (27),
 means for the rotatable mounting (25, 46, 47) of the lever (45), which mount the lever (45) rotatably between the first lever arm (48) and the second lever arm (49) on the housing (2), wherein in the lever's idle position (49) the first lever arm (48) is arranged laterally at a distance from the housing (2) and the second lever arm (49) is arranged with the cover (50) on the upper edge of the membrane element (27) so that the lever (45) through rotation of the first lever arm (48) towards the housing (2) is rotatable with the second lever arm (49) away from the displacement chamber (3) and thereby bulges a part of the membrane element (27) within its upper edge (31) upwards via the coupling element (36), and
 an insertion slot (53), which reaches from the outside up to the inside of the second lever arm (49) and extends from the free end of the second lever arm (49) up to a distance from the means for rotatable mounting (25, 46, 47), wherein the coupling rod (37) reaches through the insertion slot (53) and the head (43) of the coupling element (36) above the insertion slot (53) is supported on the outside of the cover (50),
 in which the head (43) of the coupling element (36) is inserted into a recess (55) on the outside of the cover (50), and
 in which the head (43) has the shape of a spherical cap on the outside and has together with the spherical-segment-shaped cover (50) and the on the outside spherical-segment-shaped housing part in the idle state of the lever (45) mainly the shape of a sphere.

16. The breast milk pump according to claim 1, in which the trough (56) is next to the supporting area of the head (43), into which a fingertip can be inserted in order to lift the head out of the recess (55).

17. The breast milk pump according to claim 1, in which the outlet valve (58) is a duckbill valve.

18. The breast milk pump according to claim 1, in which the outlet valve (58) is held on the lower end of a lower tube socket (12) having the outlet opening (10).

19. The breast milk pump according to claim 1, in which the cup-like membrane element (27) and/or the soft elastic insert (66) and/or the outlet valve (58) is made of a silicone elastomer.

\* \* \* \* \*